US00PP18444P3

(12) United States Plant Patent
Olesen

(10) Patent No.: US PP18,444 P3
(45) Date of Patent: Jan. 22, 2008

(54) SHRUB ROSE PLANT NAMED 'POULTC014'

(50) Latin Name: *Rosa hybrida*
Varietal Denomination: Poultc014

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/389,466

(22) Filed: Mar. 23, 2006

(65) Prior Publication Data

US 2007/0226845 P1 Sep. 27, 2007

(51) Int. Cl.
*A01H 5/00* (2006.01)

(52) U.S. Cl. ..... Plt./104

(58) Field of Classification Search ..... Plt./104
See application file for complete search history.

*Primary Examiner*—Kent Bell
*Assistant Examiner*—Louanne Krawczewicz Myers

(57) ABSTRACT

A new garden rose plant of the shrub class which has abundant, yellow flowers and attractive foliage. This new and distinct variety has shown to be uniform and stable in the resulting generations from asexual propagation.

1 Drawing Sheet

Botanical classification: *Rosa hybrida.*
Variety denomination: 'Poultc014'.

SUMMARY OF THE INVENTION

The present invention constitutes a new and distinct variety of garden rose plant which originated from a controlled crossing between the female seed parent, an unnamed seedling (non-patented), and the male pollen parent, an unnamed seedling (non-patented). The two parents were crossed during the summer of 1998, and the resulting seeds were planted in a controlled environment in Fredensborg, Denmark. The new variety is named 'Poultc014'.

The new variety may be distinguished from its seed parent, by the following combination of characteristics:

1. The claimed plant is more compact in growth height than the seed parent.
2. The claimed plant has flowers which are more deep yellow in color than those of the seed parent.

The new variety may be distinguished from the male pollen parent by the following combination of characteristics:

1. The claimed plant has smaller flowers than the pollen parent.
2. The claimed plant has more flowers per flowering stem than the pollen parent.

The objective of the hybridization of this rose variety was to create a new and distinct variety for garden use with unique qualities, such as:

1. Uniform and abundant deep yellow flowers;
2. Vigorous, but compact growth when propagated both as a budded rose and on its own roots;
3. Improved disease resistance; and
4. Suitability for container nursery culture.

This combination of qualities is not present in previously available commercial cultivars of this type, known to the inventor, and distinguish 'Poultc014' from all other varieties of which we are aware.

As part of the rose development program, Mogens N. Olesen germinated the seeds from the aforementioned hybridization during winter of 1998 and conducted evaluations on the resulting seedlings in a controlled environment in Fredensborg, Denmark.

'Poultc014' was selected in the spring 1999 by the inventor as a single plant from the progeny of the aforementioned hybridization.

Asexual reproduction of 'Poultc014' by traditional budding and rooted cuttings was first done by and Mogens N. Olesen in Fredensborg, Denmark in July, 1999. This initial and other subsequent asexual propagations conducted in controlled environments have demonstrated that the characteristics of 'Poultc014' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poultc014'. Specifically illustrated in the drawing are.

DETAILED DESCRIPTION OF THE VARIETY

Figures 1A, 1B, 1C, 1D, 1E, 1F, 1G:
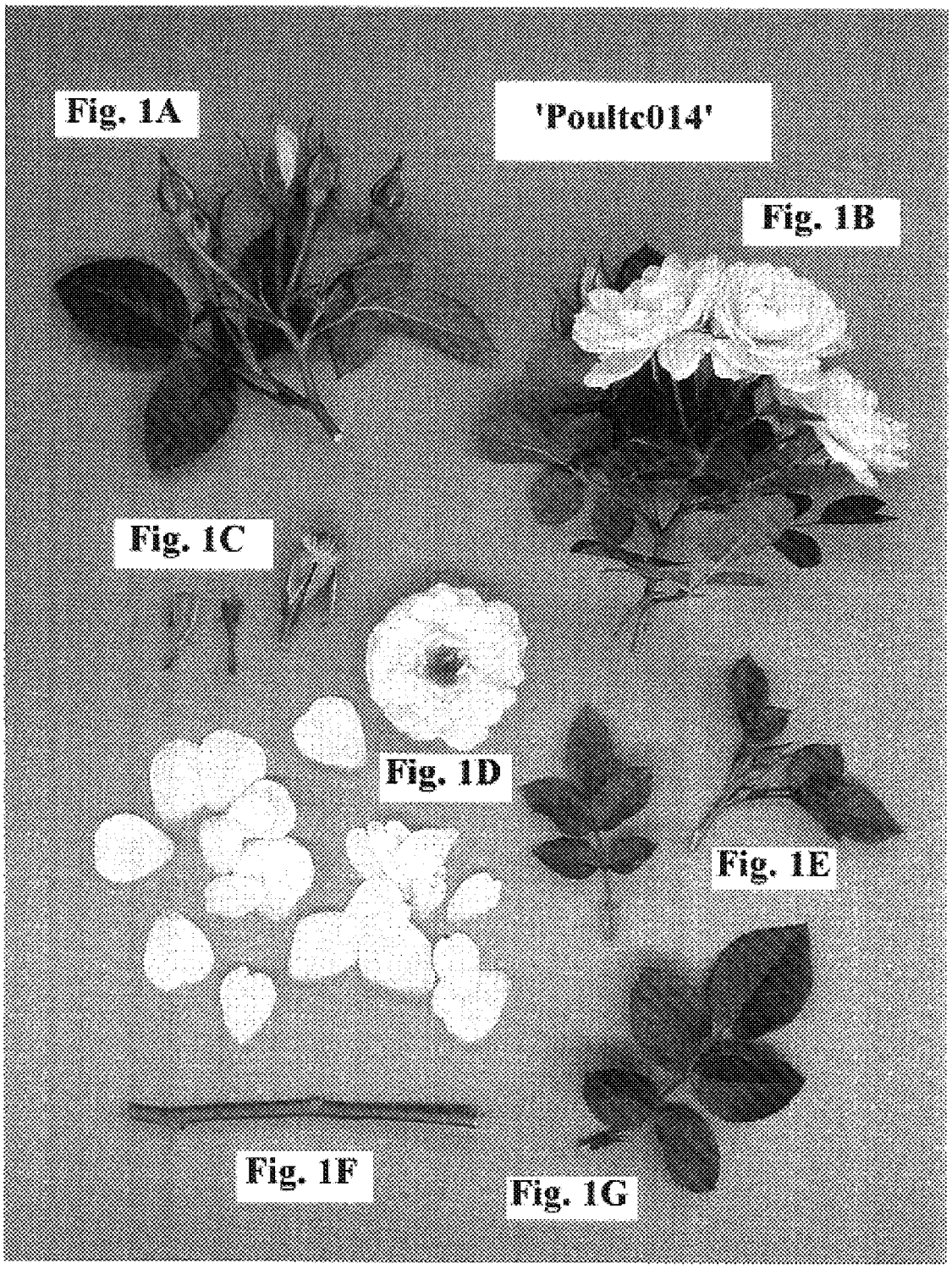
FIG. 1A Cluster of flower buds on a branch.
FIG. 1B Cluster of open flowers on a branch.
FIG. 1C Sepals, pedicel, and reproductive flower parts.
FIG. 1D Open flower and flower petals, detached.
FIG. 1E Juvenile growth and Juvenile leaf.
FIG. 1F Bare stem.
FIG. 1G Mature leaf.

The following is a description of 'Poultc014', as observed in its growth in a field nursery in Jackson County, Oreg. Observed plants are 3 years of age, grown on *Rosa multiflora* understock. Color references are made using The Royal Horticultural Society (London, England) Colour Chart, 2001, except where common terms of color are used.

For a comparison, several physical characteristics of the rose variety 'Poulgode', a rose variety from the same inventor described and illustrated in U.S. Plant patent application Ser. No. 10/782,360, now abandoned, are compared to 'Poultc014' in Chart 1.

CHART 1

| | 'Poultc014' | 'Poulgode' |
|---|---|---|
| General tonality of flower color | Yellow Group 8A to Yellow Group 10B | Yellow Group 8B to 9B to 9C |
| Length of compound leaf | 110 mm | 70 to 80 mm |
| Flower diameter | 30 mm | 35 to 45 mm |

FLOWER AND FLOWER BUD

Blooming habit: Continuous.

Flower bud:

*Size.*—Upon opening, 18 mm in length from base of receptacle to end of bud. Diameter is 8 mm.

*Bud form.*—Broad based ovoid.

*Bud color.*—As sepals unfold, petals are Yellow Group 12C. Sepal Upper Surface: Color: Green Group 138B. Surface: Medium amount of pubescence observed. Sepal Lower Surface: Color: Yellow-Green Group 146B. Texture: Mildly pubescent. Sepal Shape: Sepals are lanceolate. Apex is cirrhose. Base is flat at union with receptacle. Sepal Margin: Margins have weak foliaceous appendages on three of the five sepals and few stipitate glands. Size: Normally 17 mm (l)×5 mm (w).

*Receptacle.*—Surface: Smooth. Shape: Urn shaped. Size: 5 mm (h)×5 mm (w). Color: Yellow-Green Group 144A.

*Pedicel.*—Surface: Smooth with medium quantity of stipitate glands. Length: 15 mm average length. Diameter: 2 mm on average. Color: Yellow-Green Group 144A. Strength: Medium. Borne: On panicles consisting of 5 to 7 buds per flowering stem.

*Peduncle.*—Surface is smooth. Length is normally 7 to 25 cm. Diameter is 3 mm on average. Coloration is Yellow-Green Group 144 A.

Flower bloom:

*Fragrance.*—Light floral.

*Duration.*—The blooms have a duration on the plant of approximately 7 to 10 days. Afterwards, petals fall cleanly away from plant.

*Size.*—On average, flower diameter is 30 mm when fully open. Depth is 15 mm.

*Form.*—Open cup with petals that curve out from the center revealing reproductive flower parts.

*Shape of flower when viewed from the side.*—Upon opening, upper part: Flat. Upon opening, lower part: Flat. Open flower, upper part: Flat. Open flower, lower parts: Convex.

*Petalage.*—35 petals under normal conditions, 3 to 7 of which are petaloids.

Color:

*Upon opening, inner and outermost petals.*—Lower surface: Yellow Group 12B. Upper surface: Yellow Group 8B.

*Upon opening, basal petal spots.*—Lower surface: None. Upper surface: Yellow Group 12B.

*After opening, innermost and outermost petals.*—Lower surface: Yellow Group 12B. Upper surface: Yellow Group 8B.

*After opening, basal petal spots.*—Lower surface: None. Upper Surface: Yellow Group 12B.

General tonality: Yellow Group 8A to Yellow Group 10B. No change in tonality at the end of the 7$^{th}$ day. Afterwards, general tonality is Yellow Group 10C to Yellow Group 10D.

Petals:

*Petal reflex.*—Flat.

*Margin.*—Entire with a slight notch at the center of the apex.

*Shape.*—Generally deltoid in shape. Apex: Rounded. Base: Acute.

*Size.*—Normally 21 mm (l)×18 mm (w).

*Texture.*—Smooth.

*Thickness.*—Thin.

*Arrangement.*—Not Formal.

Petaloids:

*Quantity.*—3 to 7.

*Color.*—Upper Surface: Yellow Group 8B. Lower Surface: Yellow Group 12B.

*Size.*—On average, 15 mm (l)×5 mm (w).

*Shape.*—Irregular.

Reproductive organs:

*Pollen.*—None observed.

*Anthers.*—Size: 1 mm in length. Color: Greyed-Orange Group 167A. Quantity: 58 on average.

*Filaments.*—Color: Yellow Group 12A. Length: 5 mm.

*Stigmas.*—Level in location relative to the length of the filaments and the height of the anthers. Color: Greyed-Purple Group 183C and 183D.

*Styles.*—Color: Greyed-Green Group 193C.

*Hips.*—None Observed.

PLANT

Plant growth: Bushy, moderately low growing and compact. When grown as a budded field grown plant on *Rosa multiflora* understock, the average height of the plant is 40 to 60 cm. Average spread is 45 cm.

Stems:

*Color.*—Young wood: Yellow-Green Group 146B. Older wood: Yellow-Green Group 146B.

*Length.*—Normally 25 mm.

*Diameter.*—3 mm on average.

*Internodes.*—15 to 25 mm.

*Surface texture.*—Young wood: Smooth. Older wood: Smooth.

Prickles:

*Incidence.*—7 thorns per 10 cm of stem.

*Size.*—On average, 5 mm from base to apex. 7 mm wide.

*Color.*—Juvenile prickles: Yellow-Green Group 145A. Mature prickles: Greyed-Orange Group 173B.

*Shape.*—Upper and lower surfaces are concave.

Plant foliage: Normal number of leaflets on normal leaves in middle of the stem: 5 to 7 leaflets.

*Compound leaf size.*—Normally 110 mm (l)×50 mm (w).

*Quantity.*—3 leaves per 10 cm of stem on average.

*Color.*—Mature Foliage: Upper surface: Green Group 137A. Lower surface: Green Group 138B. Juvenile Foliage: Upper surface: Yellow-Green Group 146B. Lower surface: Yellow-Green Group 146C with intonations of Greyed-Red 178B.

Plant leaves and leaflets:

*Surface texture.*—Upper surface: Smooth. Lower surface: Smooth.

*Stipules.*—Size: 15 mm in length. Margins: Sharply serrated with few stipitate glands. Color: Yellow-Green Group 146B.

*Petiole.*—Length: 15 to 20 mm. Diameter: 1.5 mm average. Upper surface: Color: Yellow-Green Group 144A. Lower surface: Color: Yellow-Green Group 144A. Observations: Few stipitate glands and small prickles.

*Rachis.*—Length: 40 to 50 mm. Upper surface: Color: Yellow-Green Group 144A. Lower surface: Color: Yellow-Green Group 144A.

*Leaflet.*—Size: On average, 31 mm (l)×19 mm (w). Edge: Serrated. Shape: Elliptical. Base: Obtuse. Apex: Mucronate. Texture: Smooth. Thickness: Average. Arrangement: Odd pinnate. Venation: Reticulate. Glossiness: Somewhat glossy.

Disease resistance: Above average resistance to powdery and downy mildew, rust, black spot, and *Botrytis* under normal growing conditions in Jackson County, Oreg.

Cold hardiness: The variety 'Poultc014' has been found to be cold tolerant to USDA Cold Hardiness Zone 6.

It is claimed:

1. A new and distinct variety of rose plant of the shrub rose class named 'Poultc014', substantially as illustrated and described herein, due to its abundant yellow flowers, disease resistance, and extended period of bloom.

* * * * *

'Poultc014'